(12) United States Patent
Rosinko

(10) Patent No.: US 12,102,795 B2
(45) Date of Patent: Oct. 1, 2024

(54) ENHANCED CONFIRMATIONS FOR TOUCHSCREEN INFUSION PUMP

(71) Applicant: Tandem Diabetes Care, Inc., San Diego, CA (US)

(72) Inventor: Michael J. Rosinko, Anaheim, CA (US)

(73) Assignee: Tandem Diabetes Care, Inc., San Diego, CA (US)

( * ) Notice: Subject to any disclaimer, the term of this patent is extended or adjusted under 35 U.S.C. 154(b) by 131 days.

(21) Appl. No.: 17/306,022

(22) Filed: May 3, 2021

(65) Prior Publication Data

US 2021/0252218 A1 Aug. 19, 2021

Related U.S. Application Data

(63) Continuation of application No. 15/654,895, filed on Jul. 20, 2017, now Pat. No. 10,994,077.

(Continued)

(51) Int. Cl.
| | |
|---|---|
| *A61M 5/172* | (2006.01) |
| *A61M 5/142* | (2006.01) |
| *G06F 3/0484* | (2022.01) |
| *G06F 21/32* | (2013.01) |
| *G16H 20/17* | (2018.01) |
| *G16H 20/60* | (2018.01) |
| *G16H 40/63* | (2018.01) |
| *G16H 50/30* | (2018.01) |
| *A61B 5/1171* | (2016.01) |
| *A61B 5/1172* | (2016.01) |

(52) U.S. Cl.
CPC ............ *A61M 5/172* (2013.01); *A61M 5/142* (2013.01); *A61M 5/1723* (2013.01); *G06F 3/0484* (2013.01); *G06F 21/32* (2013.01); *G16H 20/17* (2018.01); *G16H 20/60* (2018.01); *G16H 40/63* (2018.01); *G16H 50/30* (2018.01); *A61B 5/1171* (2016.02); *A61B 5/1172* (2013.01); *A61M 2005/14208* (2013.01); *A61M 2205/18* (2013.01); *A61M 2205/3592* (2013.01); *A61M 2205/50* (2013.01); *A61M 2205/505* (2013.01); *A61M 2205/52* (2013.01); *A61M 2205/581* (2013.01); *A61M 2205/609* (2013.01)

(58) Field of Classification Search
CPC .............................. A61M 2205/609
See application file for complete search history.

(56) References Cited

U.S. PATENT DOCUMENTS

| | | |
|---|---|---|
| 5,482,446 A | 1/1996 | Williamson et al. |
| 5,551,850 A | 9/1996 | Williamson et al. |

(Continued)

*Primary Examiner* — Jenna Zhang

(57) ABSTRACT

Enhanced confirmations for programming of touchscreen infusion pumps reduce the likelihood of users confirming pump parameters that have been mistakenly programmed. Following programming of a given pump parameter, an icon or image intuitively related to the pump parameter can be displayed on the touchscreen. To confirm programming of the parameter, the user can be required to trace the icon on the touchscreen. The user will therefore necessarily associate the confirmation step with the parameter being programmed and be far more likely to realize if a mistake has been made because the user was intending to program a different parameter than with simple confirmations involving the press of a confirmation button.

18 Claims, 15 Drawing Sheets

Related U.S. Application Data

(60) Provisional application No. 62/365,167, filed on Jul. 21, 2016.

(56) References Cited

U.S. PATENT DOCUMENTS

| | | | |
|---|---|---|---|
| 5,782,805 | A | 7/1998 | Meinzer et al. |
| 7,004,928 | B2 | 2/2006 | Aceti et al. |
| 7,497,827 | B2 | 3/2009 | Brister et al. |
| 7,668,731 | B2 | 2/2010 | Martucci et al. |
| 7,711,402 | B2 | 5/2010 | Shults et al. |
| 7,957,984 | B1 | 6/2011 | Vallone |
| 8,231,562 | B2 | 7/2012 | Buck et al. |
| 8,287,495 | B2 | 10/2012 | Michaud et al. |
| 8,298,184 | B2 | 10/2012 | DiPerna et al. |
| 8,303,518 | B2 | 11/2012 | Aceti et al. |
| 8,311,749 | B2 | 11/2012 | Brauker et al. |
| 8,313,433 | B2 | 11/2012 | Cohen |
| 8,323,188 | B2 | 12/2012 | Tran |
| 8,337,469 | B2 | 12/2012 | Eberhart et al. |
| 8,444,595 | B2 | 5/2013 | Brukalo et al. |
| 8,449,523 | B2 | 5/2013 | Brukalo et al. |
| 8,452,953 | B2 | 5/2013 | Buck et al. |
| 8,573,027 | B2 | 11/2013 | Rosinko et al. |
| 8,601,465 | B2 | 12/2013 | Bernstein |
| 8,641,671 | B2 | 2/2014 | Michaud et al. |
| 8,758,323 | B2 | 6/2014 | Michaud et al. |
| 8,926,561 | B2 | 1/2015 | Verhoef et al. |
| 8,986,253 | B2 | 3/2015 | DiPerna |
| 9,049,982 | B2 | 6/2015 | Brukalo |
| 9,211,377 | B2 | 12/2015 | DiPerna et al. |
| 9,474,856 | B2 | 10/2016 | Blomquist |
| 9,492,608 | B2 | 11/2016 | Saint |
| 9,603,995 | B2 | 3/2017 | Rosinko et al. |
| 9,737,565 | B2 | 8/2017 | Mandel |
| 2004/0225252 | A1 | 11/2004 | Gillespie et al. |
| 2005/0022274 | A1 | 1/2005 | Campbell et al. |
| 2006/0032094 | A1 | 2/2006 | Cohen et al. |
| 2007/0016449 | A1 | 1/2007 | Cohen et al. |
| 2007/0033074 | A1 | 2/2007 | Nitzan et al. |
| 2007/0118405 | A1 | 5/2007 | Campbell et al. |
| 2008/0071580 | A1 | 3/2008 | Marcus et al. |
| 2009/0018779 | A1 | 1/2009 | Cohen et al. |
| 2009/0030733 | A1 | 1/2009 | Cohen et al. |
| 2009/0150186 | A1 | 6/2009 | Cohen et al. |
| 2010/0064257 | A1 | 3/2010 | Buck et al. |
| 2010/0095229 | A1 | 4/2010 | Dixon et al. |
| 2010/0105999 | A1 | 4/2010 | Dixon et al. |
| 2010/0174229 | A1* | 7/2010 | Hsu ............ A61M 5/142 340/5.82 |
| 2010/0274592 | A1 | 10/2010 | Nitzan et al. |
| 2010/0280486 | A1 | 11/2010 | Khair et al. |
| 2011/0126188 | A1 | 5/2011 | Bernstein et al. |
| 2011/0144586 | A1* | 6/2011 | Michaud ........ A61M 5/31513 604/151 |
| 2011/0144616 | A1* | 6/2011 | Michaud ............ F16J 15/56 604/153 |
| 2011/0152770 | A1 | 6/2011 | DiPerna et al. |
| 2011/0201911 | A1 | 8/2011 | Johnson |
| 2012/0004932 | A1* | 1/2012 | Sorkey ............... G16H 10/60 705/3 |
| 2012/0030610 | A1 | 2/2012 | DiPerna et al. |
| 2012/0059673 | A1 | 3/2012 | Cohen et al. |
| 2012/0232520 | A1 | 9/2012 | Sloan et al. |
| 2013/0053816 | A1 | 2/2013 | DiPerna et al. |
| 2013/0131630 | A1 | 5/2013 | Blomquist |
| 2013/0324928 | A1 | 12/2013 | Kruse |
| 2013/0331790 | A1 | 12/2013 | Brown et al. |
| 2013/0332874 | A1* | 12/2013 | Rosinko ............ G16H 40/63 715/771 |
| 2014/0276420 | A1 | 9/2014 | Rosinko |
| 2014/0276531 | A1 | 9/2014 | Walsh |
| 2014/0276556 | A1 | 9/2014 | Saint et al. |
| 2014/0331175 | A1* | 11/2014 | Mesguich Havilio ............ G06F 3/0481 715/863 |
| 2015/0182693 | A1 | 7/2015 | Rosinko |
| 2015/0314062 | A1 | 11/2015 | Blomquist et al. |
| 2016/0014584 | A1* | 1/2016 | Webb ................. H04W 4/90 455/404.2 |
| 2016/0082188 | A1 | 3/2016 | Blomquist et al. |
| 2016/0339172 | A1 | 11/2016 | Michaud et al. |
| 2017/0056590 | A1 | 3/2017 | DiPerna et al. |
| 2019/0088353 | A1* | 3/2019 | Humphrys ........... G16H 40/63 |

\* cited by examiner

ENHANCED CONFIRMATIONS FOR TOUCHSCREEN INFUSION PUMP

RELATED APPLICATIONS

This application is a continuation of application Ser. No. 15/654,895 filed Jul. 20, 2017, which claims the benefit of U.S. Provisional Application No. 62/365,167 filed Jul. 21, 2016, each of which is hereby incorporated herein in its entirety by reference.

TECHNICAL FIELD

The present invention is directed to portable infusion pumps and more particularly to user interfaces for programming and confirming programming for portable infusion pumps.

BACKGROUND

There are many applications in academic, industrial, and medical fields that benefit from devices and methods that are capable of accurately and controllably delivering fluids, such as liquids and gases, that have a beneficial effect when administered in known and controlled quantities. Such devices and methods can be particularly useful in the medical field where treatments for many patients include the administration of a known amount of a substance at predetermined intervals.

One category of devices for delivering such fluids is that of insulin injecting pumps that have been developed for the administration of insulin for those suffering from both type I and type II diabetes. Some insulin injecting pumps configured as portable infusion devices can provide continuous subcutaneous insulin injection and/or infusion therapy for the treatment of diabetes. Such therapy may include the regular and/or continuous injection or infusion of insulin into the skin of a person suffering from diabetes and offer an alternative to multiple daily injections of insulin by an insulin syringe or an insulin pen. Such pumps can be ambulatory/portable infusion pumps that are worn by the user and may use replaceable cartridges. Such pumps can also deliver medicaments other than or in addition to insulin, such as glucagon, pramlintide, etc. Examples of such pumps and various features that can be associated with such pumps include those disclosed in U.S. Patent Application Publication No. 2013/0053816, U.S. Pat. Nos. 8,573,027, 8,986,253, U.S. Patent Application Publication No. 2013/0324928, U.S. Patent Application Publication No. 2013/0331790, U.S. Pat. No. 8,287,495 and U.S. patent application Ser. No. 15/158,125, each of which is hereby incorporated herein by reference in its entirety.

Some ambulatory medical devices include a touchscreen on which symbols may be displayed and from which inputs may be received for operation of the device. Other input mechanisms involve keyboards or hardware switches. In general, a series of display screens or windows are shown on a device display or on the device touchscreen, showing alphanumeric text and symbols, and providing menu screens through which the user can control operation of the device.

With the proliferation of handheld electronic devices, such as mobile phones (e.g., smartphones), there is a desire to be able to remotely utilize such devices, as well as dedicated wireless controllers designed to work with one or more infusion pumps and/or types of infusion pumps, to optimize usage of infusion pumps. Infusion pumps are often discreetly located on or around a patient, such as beneath clothing or in a carrying pouch. Some infusion pumps are therefore adapted to be programmed and/or controlled with remote devices that enable programming and/or control without directly interacting with a user interface located on the pump. These remote controllers therefore enable a pump to be monitored, programmed and/or operated more privately, more conveniently and more comfortably. Accordingly, one potential use of dedicated remote devices and handheld consumer electronic devices (such as smartphones, tablets and the like) is to utilize such devices as controllers for remotely programming and/or operating infusion pumps.

Infusion pumps are therefore controlled through user interactions with a user interface, whether a user interface of the pump itself or of a remote device such as a dedicated remote control or a smartphone. These interactions can be responsible for programming and/or activating device functions relating to initiating, suspending and changing insulin or other medicament delivery and for monitoring the status of pump operations, blood glucose levels (if working with glucose monitors) and historical data related to the pump and the user, to name a few, and are therefore critically important for medicament therapy and patient health and safety. As such, many programming operations require a user to provide a confirmation following programming before the programmed instructions are executed by the pump. Such a confirmation typically is provided in the form of a user selecting a "YES" or check mark icon to confirm or a "NO" or "X" icon to cancel. However, human factors testing has shown that when patients become familiar with the user interface of a given device, they quickly go through confirmations without properly reviewing the entered programming instructions. This can be especially acute when the user interface is a touchscreen, given the mechanical ease with which an interaction can be made and the familiarity of users with such interfaces due to the ubiquity of smartphones, tablet computers, and other touchscreen interfaces in many people's daily lives. As such, there is a need for alternate means by which patients can confirm programming of pump parameters and settings that will inherently require patients to be more observant of the parameters and settings that are being confirmed.

SUMMARY

Enhanced confirmations for programming of touchscreen infusion pumps reduce the likelihood of users confirming pump parameters that have been mistakenly programmed. Following programming of a given pump parameter, a pictorial icon or image intuitively related to the pump parameter can be displayed on the touchscreen. To confirm programming of the parameter, the user can be required to trace the icon on the touchscreen. The user will therefore necessarily associate the confirmation step with the parameter being programmed and be far more likely to realize if a mistake has been made because the user was intending to program a different parameter than with simple confirmations involving the press of a confirmation button.

In one embodiment, a method of delivering medicament to a user with a portable infusion pump includes displaying a bolus setup page on a touch-screen display of a portable infusion pump system and receiving a user entry of a value for a pump parameter for calculation of a bolus of medicament to be delivered to the user via the bolus setup page. A confirmation screen can then be displayed on the touch-screen display requiring a confirmation of the user entry and including a pictorial icon representing the pump parameter. When a user interaction with the touch-screen display of the user tracing an outline of the pictorial icon is identified, the interaction is used as a confirmation of the pump parameter. The portable infusion pump can then be caused to deliver the bolus of medicament to the user after identifying the confirmation of the user tracing the outline of the pictorial icon.

In one embodiment, a portable infusion pump includes a reservoir configured to contain a medicament, a pumping mechanism configured to deliver medicament from the reservoir to a user and a user interface including a touch-screen display. A processor of the pump is programmed to display a bolus setup page on the touch-screen display and receive a user entry of a value for a pump parameter for calculation of a bolus of medicament to be delivered to the user via the bolus setup page. The processor is further programmed to display a confirmation screen on the touch-screen display requiring a confirmation of the user entry that includes a pictorial icon representing the pump parameter. The processor can identify a user interaction with the touch-screen display as the user providing the confirmation by tracing an outline of the pictorial icon and then cause the pumping mechanism to deliver the bolus of medicament to the user.

The above summary is not intended to describe each illustrated embodiment or every implementation of the subject matter hereof. The figures and the detailed description that follow more particularly exemplify various embodiments.

BRIEF DESCRIPTION OF THE DRAWINGS

Subject matter hereof may be more completely understood in consideration of the following detailed description of various embodiments in connection with the accompanying figures, in which.

Figure 1:
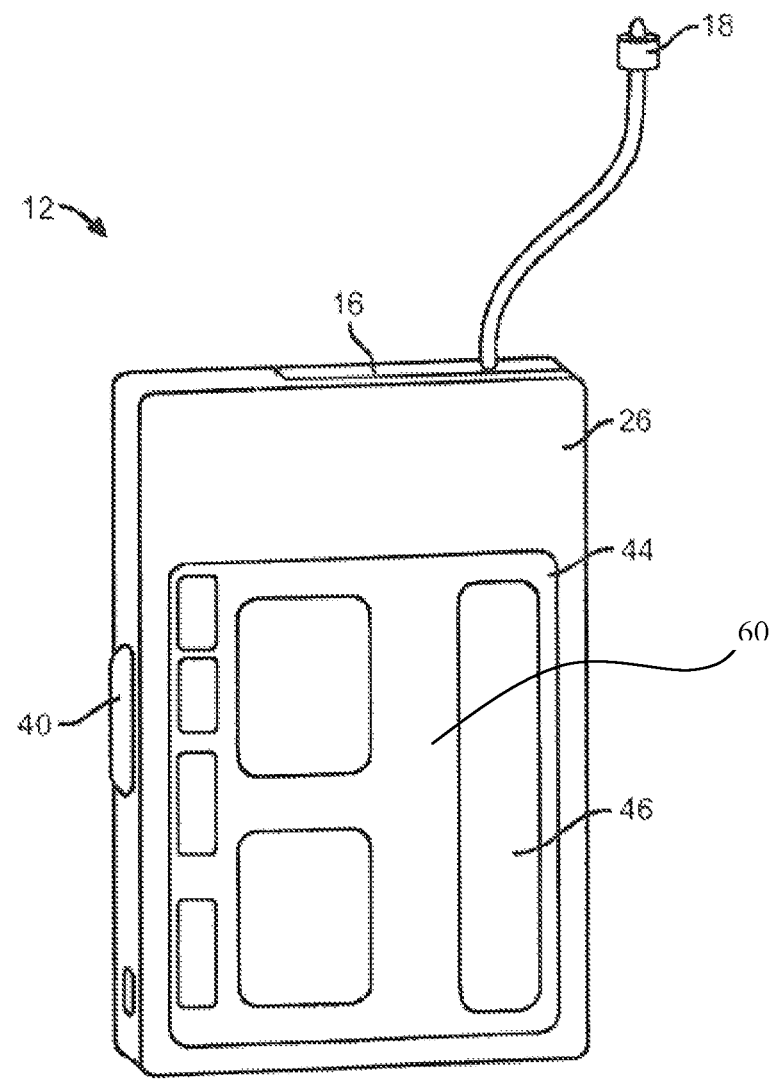
FIG. 1 is a medical device that can be used with embodiments of the present invention.

While various embodiments are amenable to various modifications and alternative forms, specifics thereof have been shown by way of example in the drawings and will be described in detail. It should be understood, however, that the intention is not to limit the claimed inventions to the particular embodiments described. On the contrary, the intention is to cover all modifications, equivalents, and alternatives falling within the spirit and scope of the subject matter as defined by the claims.

DETAILED DESCRIPTION OF THE DRAWINGS

The following detailed description should be read with reference to the drawings in which similar elements in different drawings are numbered the same. The drawings, which are not necessarily to scale, depict illustrative embodiments and are not intended to limit the scope of the invention.

FIG. 1 depicts an exemplary medical device that can be used with embodiments of the present invention. In this embodiment, the medical device is configured as a pump 12, such as an infusion pump, that can include a pumping or delivery mechanism and reservoir for delivering medicament to a patient and an output/display 44. The type of output/display 44 may vary as may be useful for a particular application. When visual, output/display 44 may include LCD displays, LED displays, plasma displays, graphene-based displays, OLED displays and the like. The output/display 44 may include an interactive and/or touch sensitive screen 46 having an input device such as, for example, a touch screen comprising a capacitive screen or a resistive screen. The pump 12 may additionally include a keyboard, microphone, or other input device known in the art for data entry, which may be separate from the display. The pump 12 may also include a capability to operatively couple to one or more blood glucose meters (BGMs) or continuous blood glucose monitors (CGMs) and/or one or more secondary display devices such as a remote display, a remote control device, a laptop computer, personal computer, tablet computer, a mobile communication device such as a smartphone, a wearable electronic watch or electronic health or fitness monitor, or personal digital assistant (PDA), etc.

In one embodiment, the medical device can be a portable pump configured to deliver insulin to a patient. Further details regarding such pump devices can be found in U.S. Pat. No. 8,287,495, which is incorporated herein by reference in its entirety. In other embodiments, the medical device can be an infusion pump configured to deliver one or more additional or other medicaments to a patient. In a further embodiment, the medical device can be a glucose meter such as a BGM or CGM. Further detail regarding such systems and definitions of related terms can be found in, e.g., U.S. Pat. Nos. 8,311,749, 7,711,402 and 7,497,827, each of which is hereby incorporated by reference herein in its entirety. In other embodiments, the medical device can monitor other physiological parameters of a patient.

Figure 2:
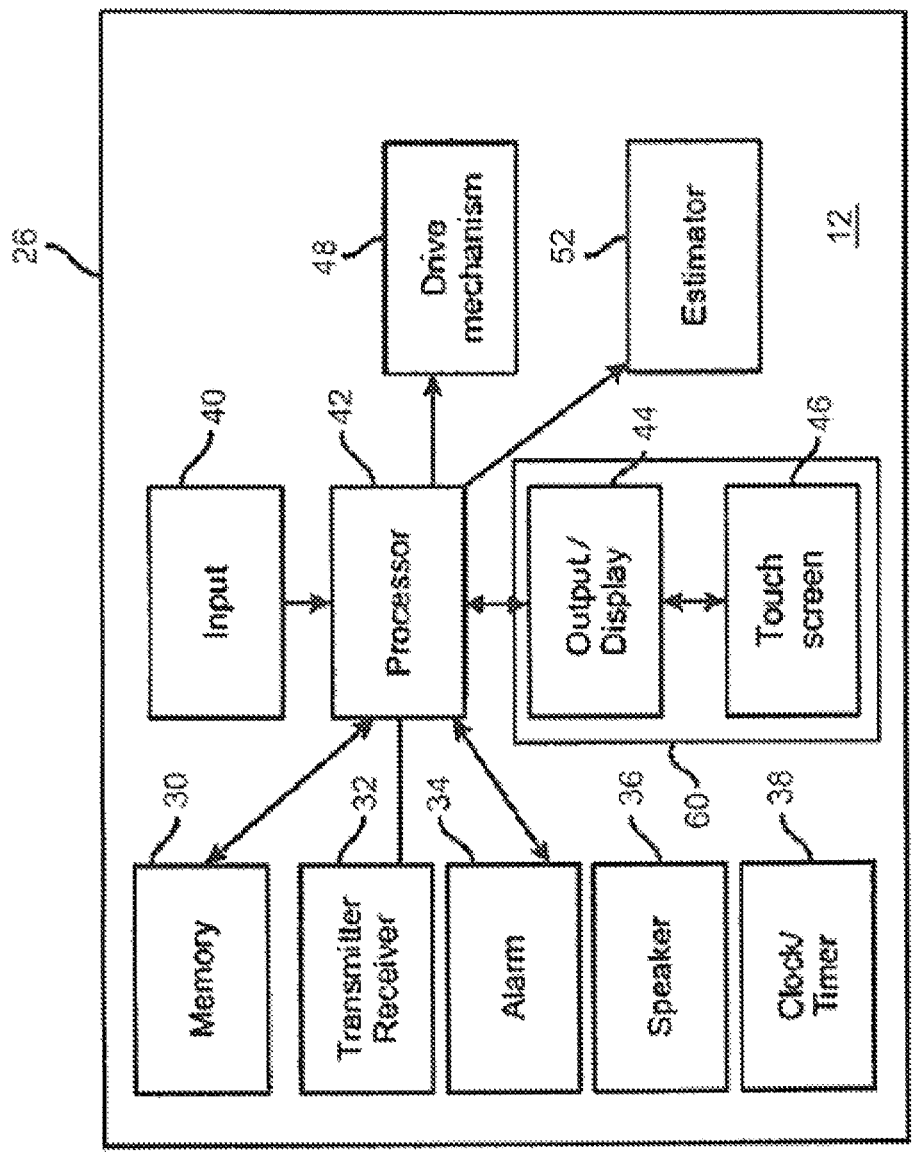
FIG. 2 is a block diagram representing a medical device that can be used with embodiments of the present invention.

FIG. 2 illustrates a block diagram of some of the features that can be used with embodiments of the present invention, including features that may be incorporated within the housing 26 of a medical device such as a pump 12. The pump 12 can include a processor 42 that controls the overall functions of the device. The infusion pump 12 may also include, e.g., a memory device 30, a transmitter/receiver 32, an alarm 34, a speaker 36, a clock/timer 38, an input device 40, a user interface suitable for accepting input and commands from a user such as a caregiver or patient, a drive mechanism 48, an estimator device 52 and a microphone (not pictured). One embodiment of a user interface as shown in FIG. 2 is a graphical user interface (GUI) 60 having a touch sensitive screen 46 with input capability. In some embodiments, the processor 42 may communicate with one or more other processors within the pump 12 and/or one or more processors of other devices, for example, a continuous glucose monitor (CGM), display device, smartphone, etc.

through the transmitter/receiver. The processor 42 may also include programming that may allow the processor to receive signals and/or other data from one or more input devices, such as sensors that may sense pressure, temperature and/or other parameters.

Figure 3:
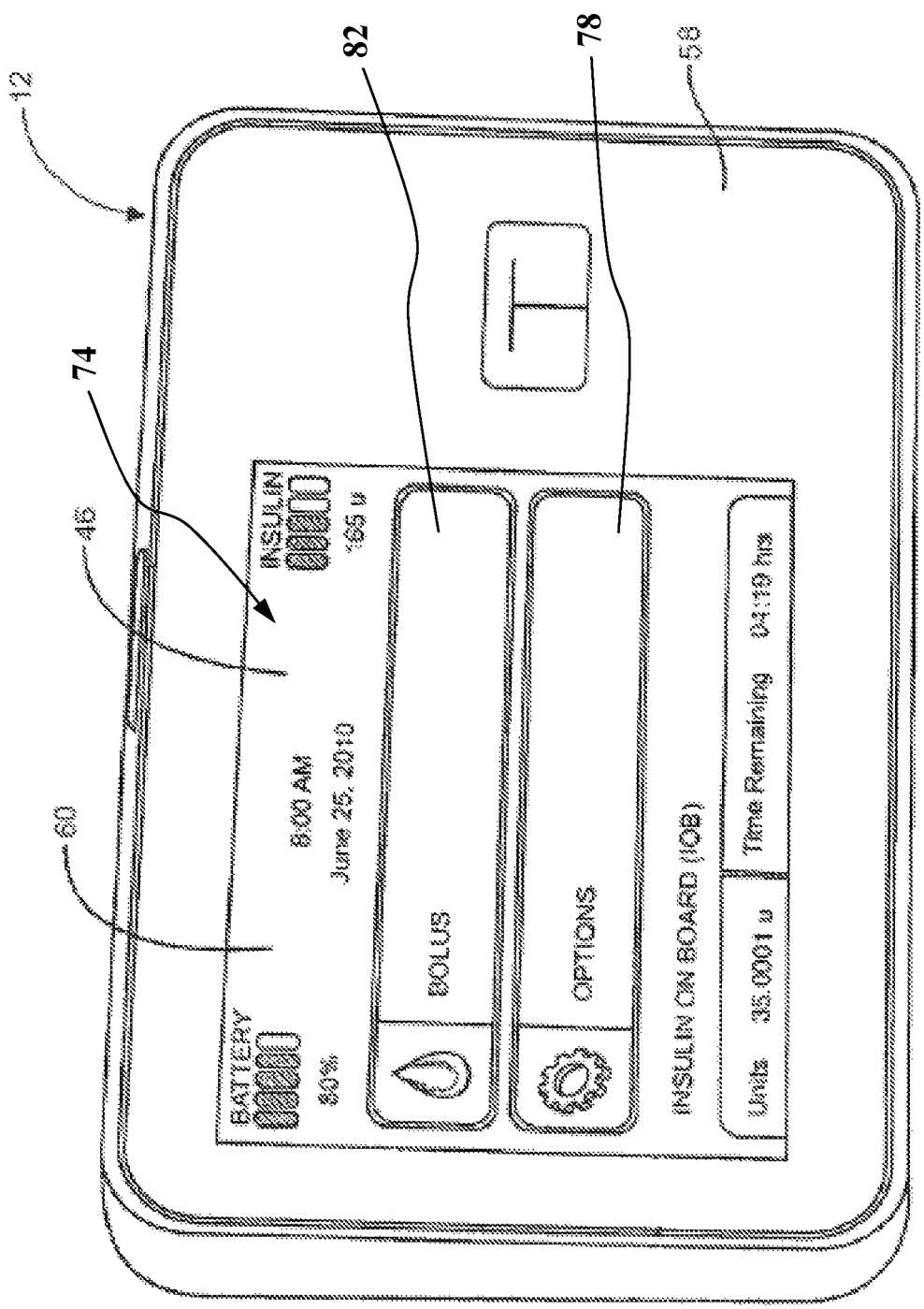
FIG. 3 depicts an exemplary home screen page of a user interface of an infusion pump that can be used with embodiments of the present invention.

Referring to FIG. 3, a front perspective view of pump 12 is depicted. Pump 12 may include a user interface, such as, for example, a GUI 60 on a front surface 58 or other location of pump 12. GUI 60 may include a touch-sensitive screen 46 that may be configured for displaying data, facilitating data and/or command entry, providing visual tutorials, as well as other interface features that may be useful to a caregiver or to the patient operating pump 12. The GUI can also present alarms or alerts to the user. Depicted on the GUI 60 in FIG. 3 is one embodiment of a home screen page 74 for a user interface of a pump 12. Home screen 74 can display various status information pertaining to pump 12 and can include a touch selectable options object 78 through which the user can access various options pertaining to pump 12 and a touch selectable bolus object 82. Bolus object 82 is selectable by the user to initiate execution of a bolus delivery program that enables a user to setup a bolus delivery of insulin with pump 12. The bolus delivery program may include a bolus workflow or protocol which may, in combination with the processor 42 and memory 30 of the pump 12, present the user with pages or screen representations having a number of queries and information for setting up an appropriate bolus of insulin to be delivered to the user.

Figure 4A:
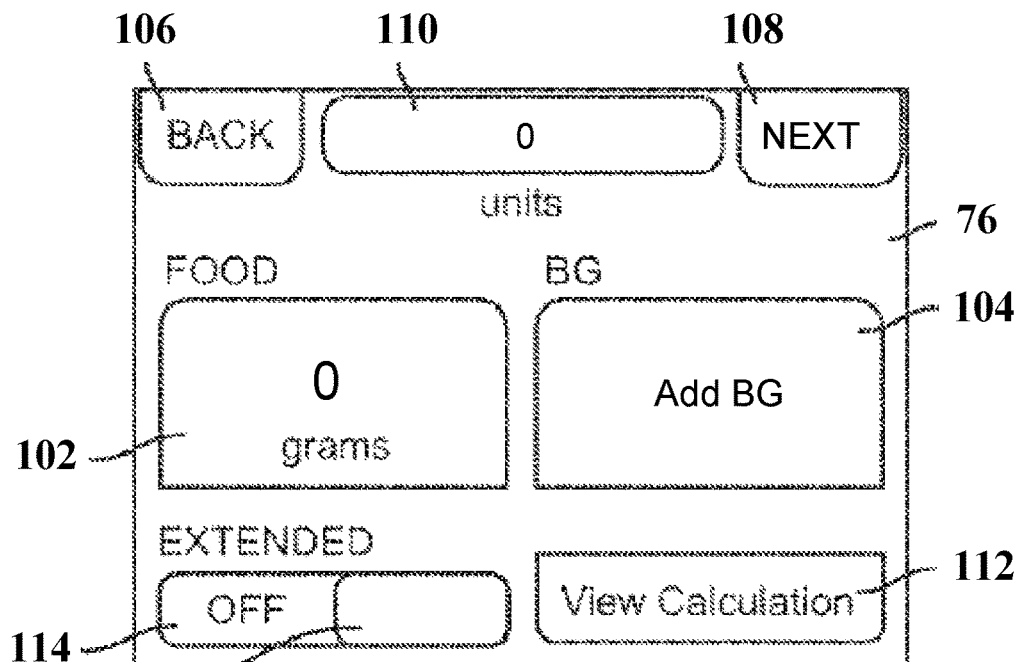
FIGS. 4A-4C and 5A-5C depict exemplary bolus programming screens according to embodiments of the present invention.
Figure 4B:
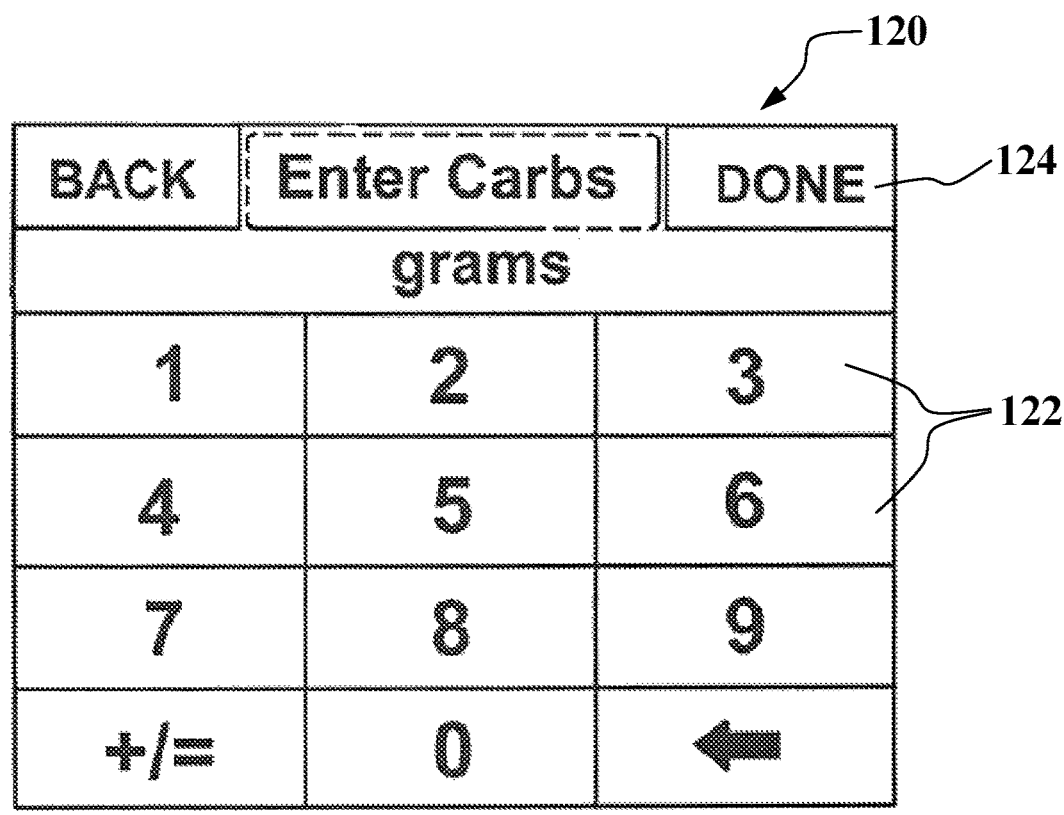
Figure 4C:
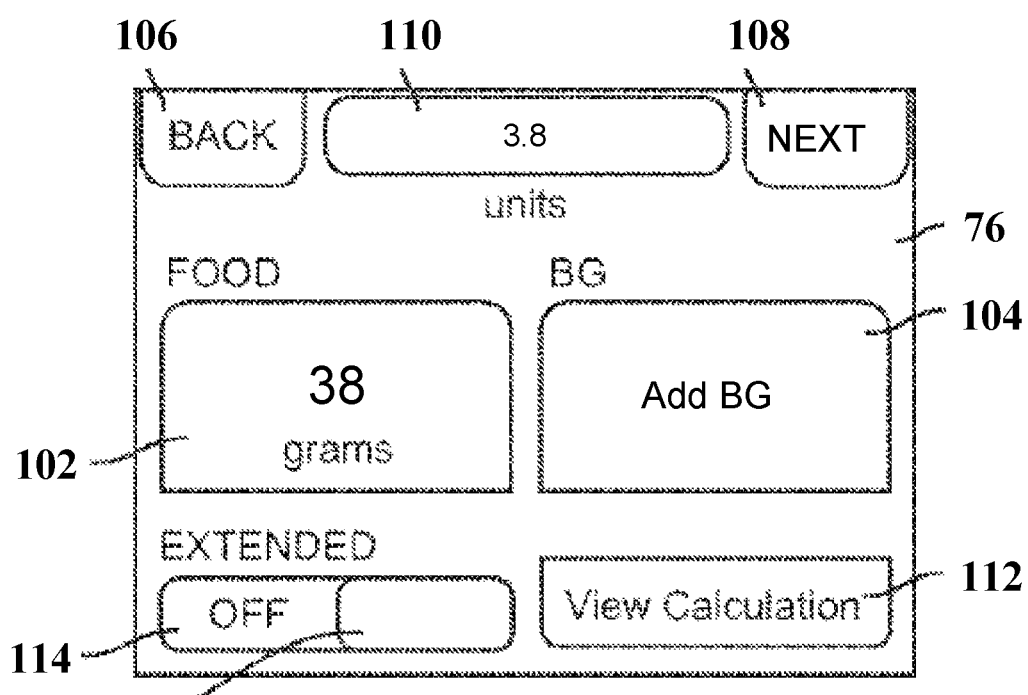

FIGS. 4A-4C depict a bolus programming procedure that can be used to program a bolus of medicament such as insulin for delivery to a user with pump 12 according to an embodiment of the present invention. A bolus setup page 76 that can be displayed on pump 12 following selection of the BOLUS object 82 on the home screen 74 is depicted in FIG. 4A. Bolus setup page 76 can include a FOOD BOLUS object 102 and a BLOOD GLUCOSE (BG) object 104. A BACK object 106 can be selected to navigate back to the previous menu screen. A slider 116 can be used to set whether or not delivery of the bolus will be by an extended bolus, as is known in the art. In the depicted embodiment, the extended bolus is set to the OFF object 114.

The FOOD BOLUS object 102 is selectable to enable a user to enter a number of grams of carbohydrates a user has consumed or intends to consume via a virtual keypad 120 that is displayed on the GUI when the FOOD BOLUS object 102 is selected. After a user enters a number of carbohydrates using the keys 122 of the virtual keypad 120, an object 124 representing the user's confirmation that the previous step has been completed (shown in the embodiment of FIG. 4B as a DONE object) can be selected to return to the bolus setup page 76. The setup page, as shown in FIG. 4C, now displays both the amount of carbohydrates entered, in this embodiment 38 grams, into the FOOD BOLUS object 102 and the units of insulin calculated by the device for delivery—based on the entered carbohydrate amount and a stored insulin sensitivity factor—in an INSULIN UNITS object 110. The calculations behind the determination of the number of insulin units can be viewed by selecting a VIEW CALCULATION object 112. An ADD BG object 104 can further be selected to enable the device to calculate whether an additional correction bolus should be delivered based on a blood glucose level of the user entered via the ADD BG object 104, as is known in the art. Once a user has entered all desired values for programming a bolus delivery, the NEXT object 108 may be selected.

Figure 5A:
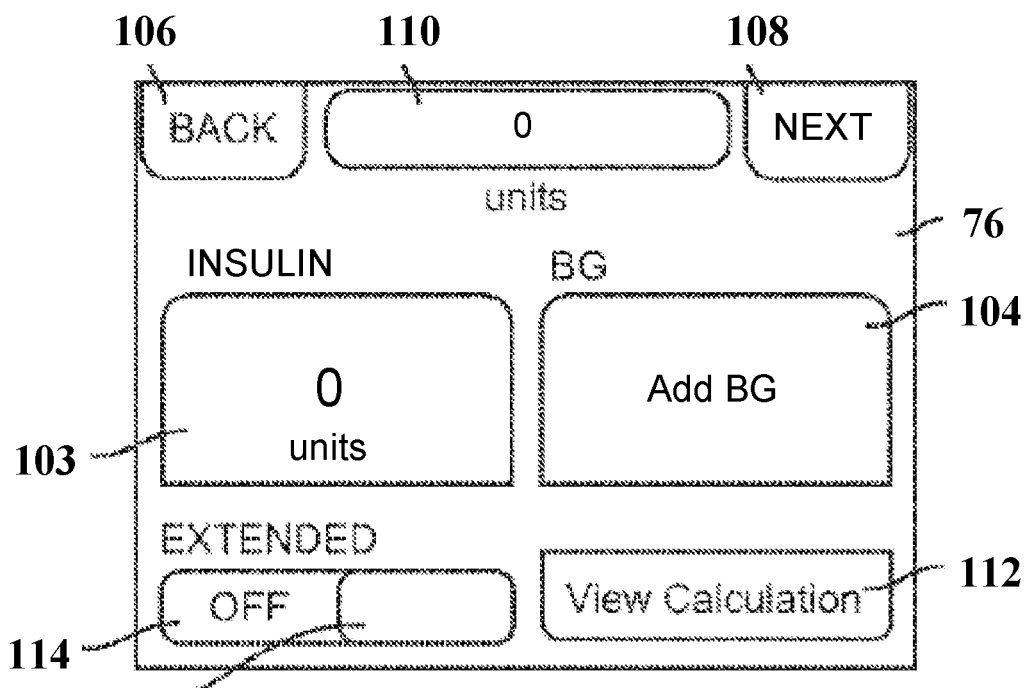
Figure 5B:
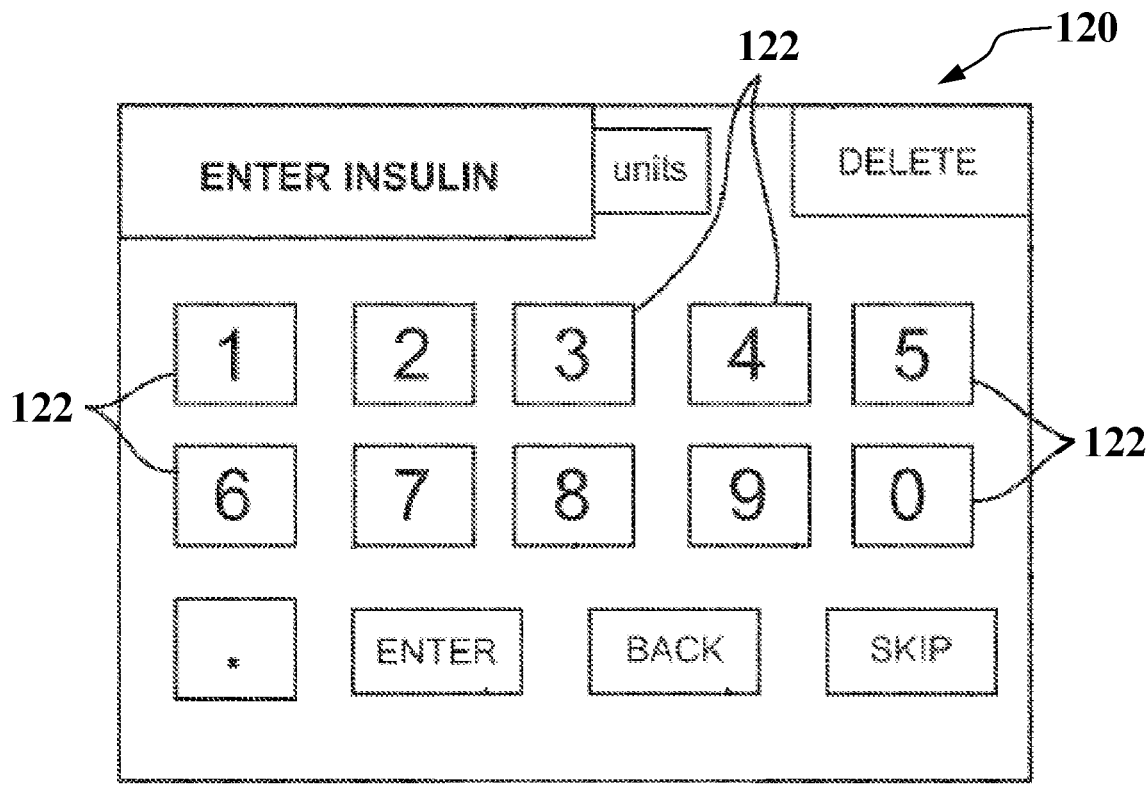
Figure 5C:
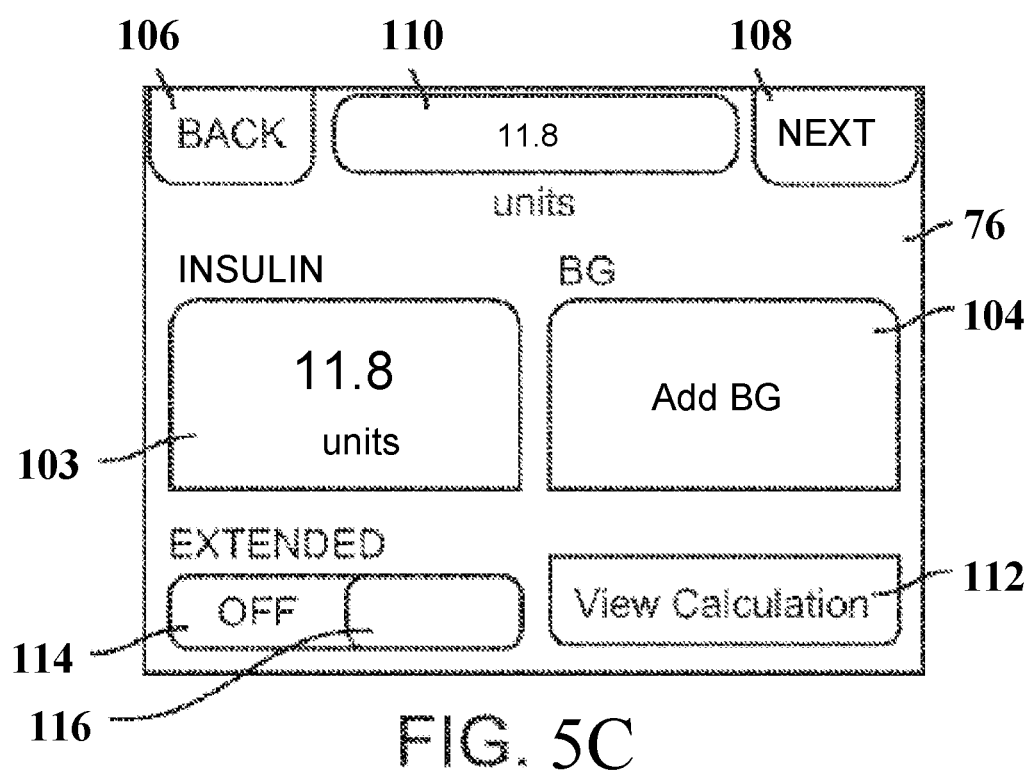
Figure 6A:
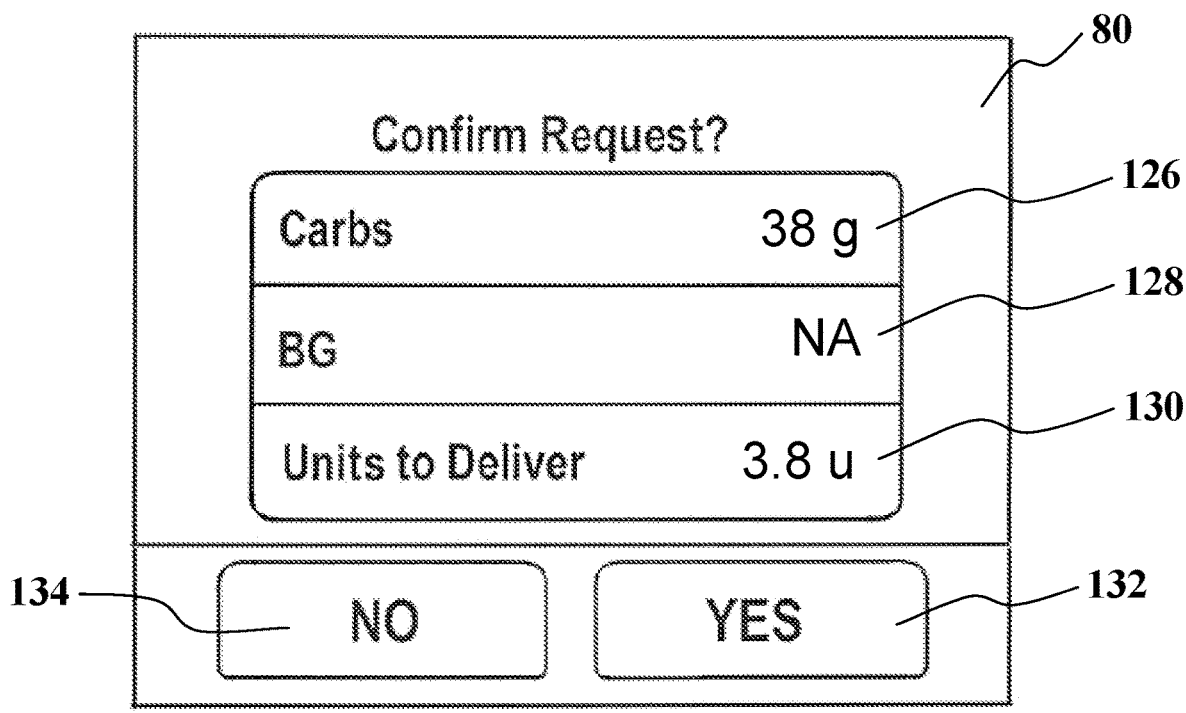
FIGS. 6A-6B and 7A-7B depict prior art bolus confirmation screens.
Figure 6B:
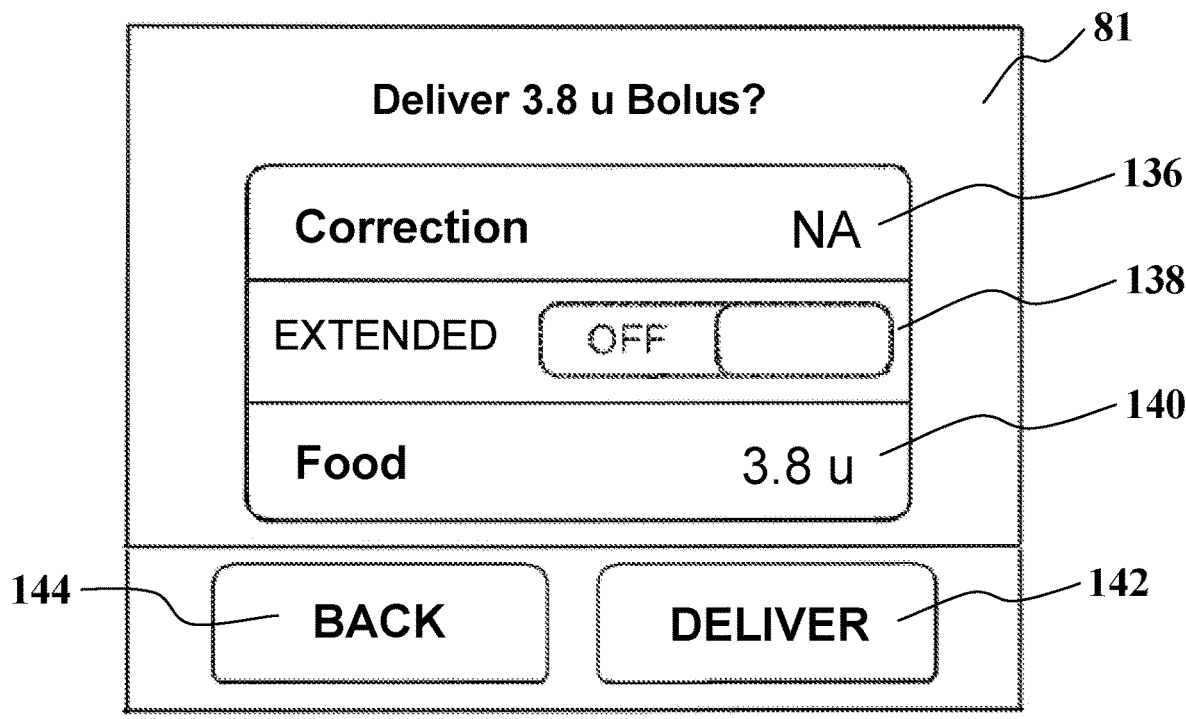
Figure 7A:
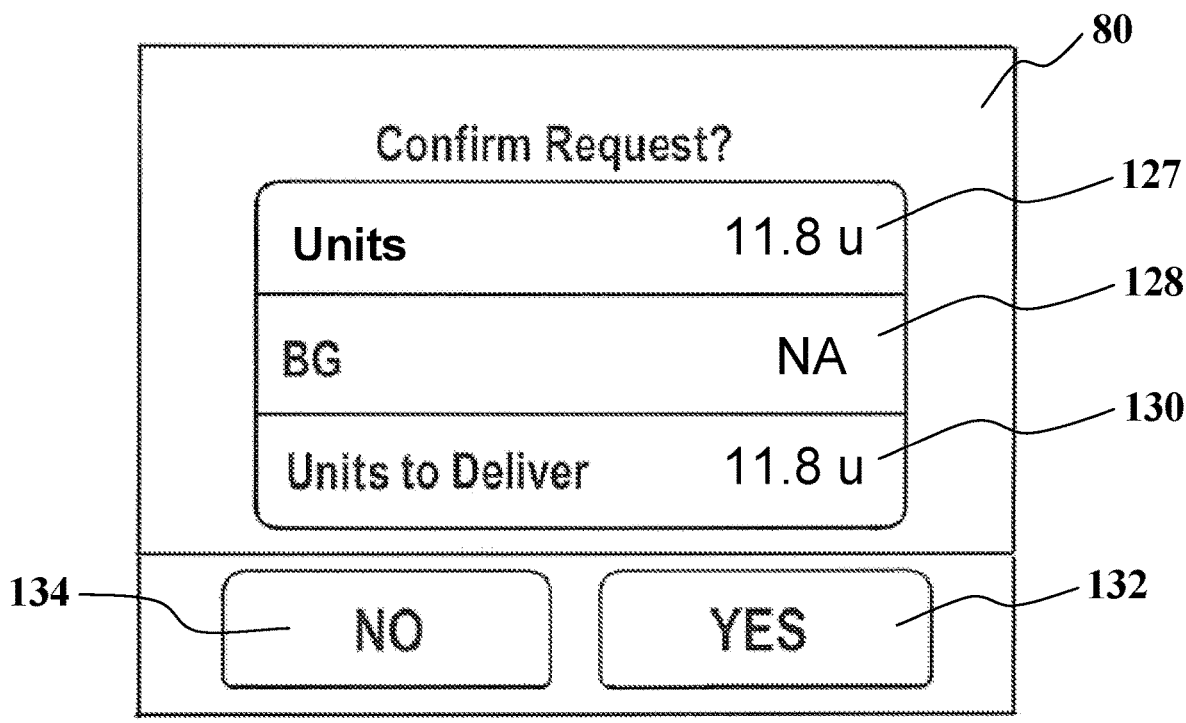
Figure 7B:
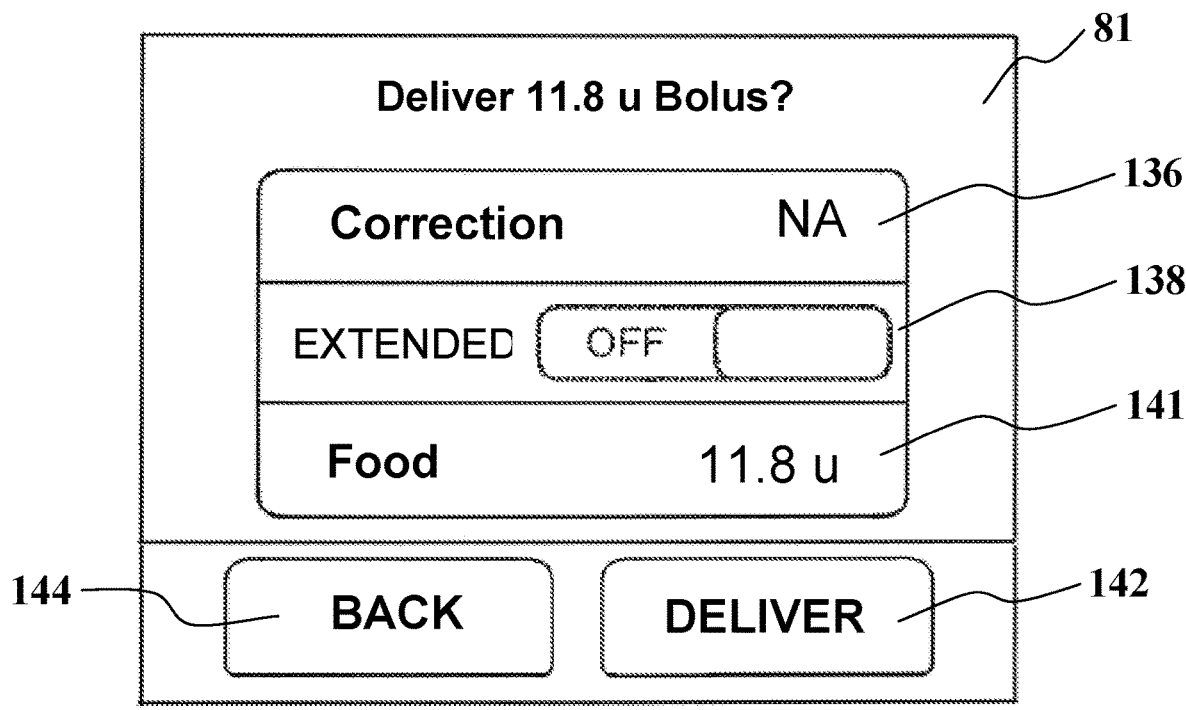

FIGS. 5A-5C depict another embodiment of a bolus programming procedure. In this embodiment, rather than entering a number of carbohydrates and having the device calculate a corresponding number of units of insulin, the user directly enters the number of units of insulin for delivery in the bolus by selecting an INSULIN BOLUS object 103.

Following selection of the NEXT object 108, pump 12 can require a user to confirm the bolus through the GUI. A prior art procedure for confirming such boluses is depicted in FIGS. 6A-6B and FIGS. 7A-7B. A first confirmation page 80 is displayed after selection of the next object 108, on which either the entered number of carbohydrates 126 (FIG. 6A) or the entered units of insulin 127 (FIG. 7A) is displayed, along with a blood glucose level 128 if one was entered and a total number of units of insulin to be delivered 130, which is calculated as the sum of the carbohydrate/insulin bolus and any correction bolus. A user can confirm the bolus by selecting a YES object 132 or cancel and return to a previous screen by selecting a NO object 134. If the user selects the YES object 132, a second confirmation page 81 can appear displaying the number of units to be delivered based on the correction bolus 136 (none in this example) and the number of units to be delivered based on either the carbohydrate bolus 140 (FIG. 7A) or the insulin bolus 141 (FIG. 7B), along with whether or not the bolus is to be delivered as an extended bolus 138. The user can again return to a previous screen by selecting a BACK object 144. Selecting the DELIVER object 142 provides a second confirmation that causes the pump 12 to proceed with the bolus delivery.

Although the use of dual-confirmation screens as described with respect to FIGS. 6A-6B and FIGS. 7A-7B provides some measure of security against mistakes in programming boluses, as discussed above, human factors testing has shown that as users become more comfortable and used to using such interfaces, they have a tendency to quickly tap objects such as the YES object 132 on the first confirmation page 80 and the DELIVERY object 142 on the second confirmation page 82 without adequately or actually reviewing the data on these screens to ensure that the bolus has been properly programmed. For example, if a user mistakenly selected the INSULIN BOLUS object 103 and entered "38" thinking the user was entering grams of carbohydrates rather than units of insulin, users may have the tendency to click through the confirmation objects, screens, etc. without realizing the wrong parameter was entered, the result of which can lead to serious medical consequences. Similarly, although different units are used, typical numerical values representing the amounts of carbohydrates in a meal or a serving of food, e.g., 120 grams, can be in the same or within a similar range to those of typical blood glucose levels, e.g., 120 mg/dL, making such errors particularly possible in such situations where different parameters can have the same numerical values. For example, in the described example of carbohydrates and blood glucose levels, a typical range of blood glucose levels may be between 80 mg/dL and 180 mg/dL whereas a typical range of carbohydrates in a meal or a food serving may be between 50 grams and 150 grams, and such overlapping ranges lead to common numerical values that may be appropriate for either parameter. As such, embodiments of the present invention employ more robust confirmation procedures and methods to ensure a user has a greater understanding of the parameters which the user is confirming.

Figure 8A:
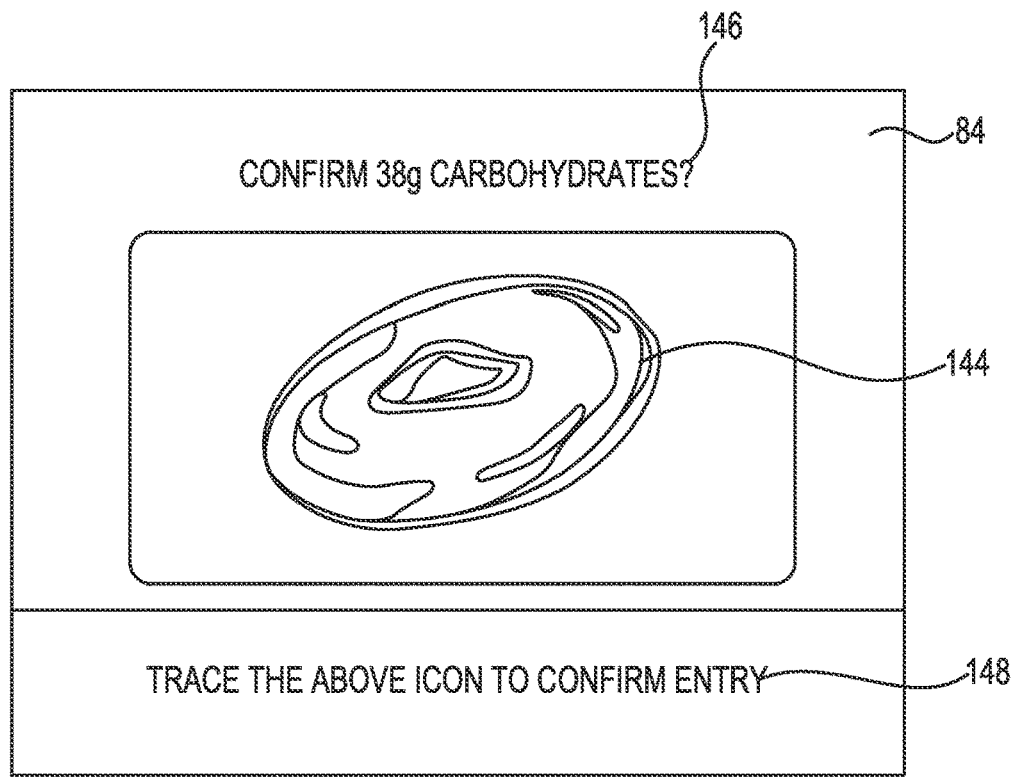
FIGS. 8A-8B, 9A-9B and 10A-10B depict exemplary confirmation screens according to embodiments of the present invention.
Figure 8B:
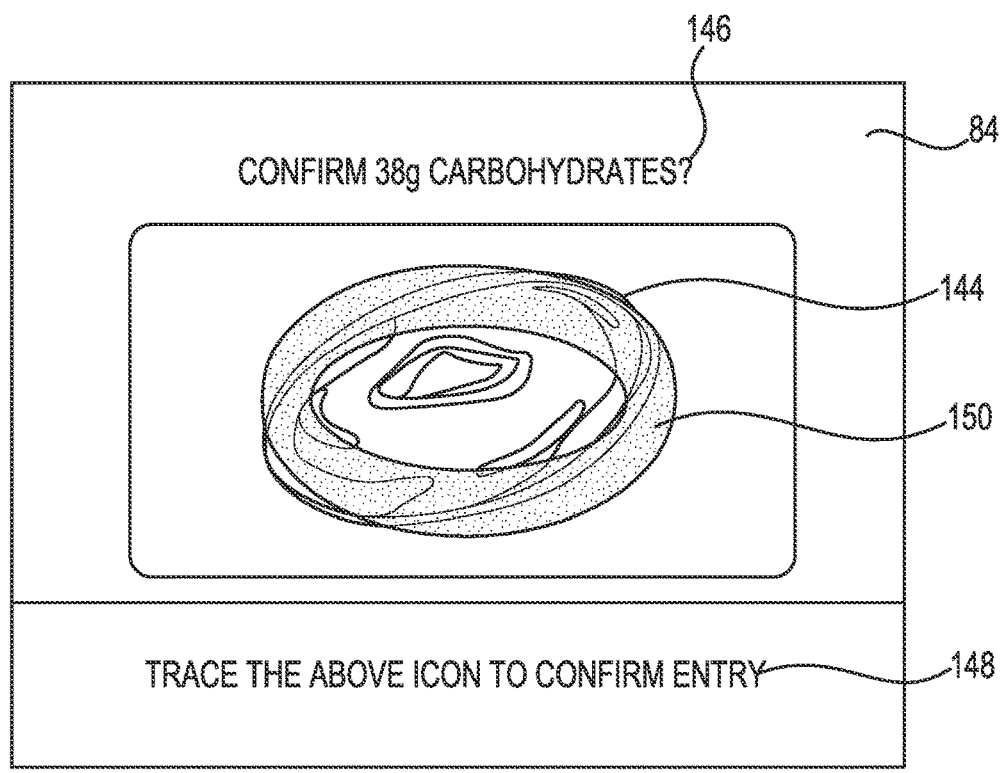

FIGS. 8A-8B depict an example confirmation screen 84 that can be utilized in confirming entry of carbohydrate values into an infusion pump according to embodiments of the present invention. In this embodiment, a pictorial icon 144 depicting a bagel is utilized, but a pictorial icon of any other item of food or other image, letter, word, audible prompt (delivered, e.g., through speaker 36), video clip, graphics file (e.g., GIF), vibratory alert (delivered through a vibratory element), biometric input (e.g., fingerprint or retinal confirmation), orientation/acceleration (via, e.g., a gyroscope and/or accelerometer) or multiple instances of and/or combinations of the aforementioned, possibly timed in a way to optimize the user's attention, to represent the idea of food consumption in this context could be utilized. Carbohydrate confirmation screen 84 can include confirmation text 146 and/or another type of visual and/or audible confirmation specifying the parameter being confirmed, in this case entry of 38 grams of carbohydrates, and instruction text 148 (and/or other vehicle or technique noted above) informing the user how to submit a confirmation. The confirmation is submitted by the user tracing the icon 144 on the touchscreen interface. FIG. 8B depicts one example tracing pattern 150 that provides the confirmation. As shown in the figure, tracing patterns such as tracing pattern 150 need not necessarily exactly match the outline of the icon 144. In addition, in one embodiment the tracing pattern of each icon would be different from the tracing pattern of each other icon to further help avoid possible accidental confirmation. The processor of the device can include logic for determining to what extent a gesture made on the screen can be considered an icon trace representing a confirmation. In various embodiments, carbohydrate confirmation screen 84 can be displayed after selecting the FOOD BOLUS object 102 and entering a carbohydrate amount via the keypad 120, as a first confirmation screen prior to bolus delivery in place of or in conjunction with first confirmation screen 80, as a second confirmation screen prior to bolus delivery in place of or in conjunction with second confirmation screen 81, or some combination thereof.

Figure 9A:
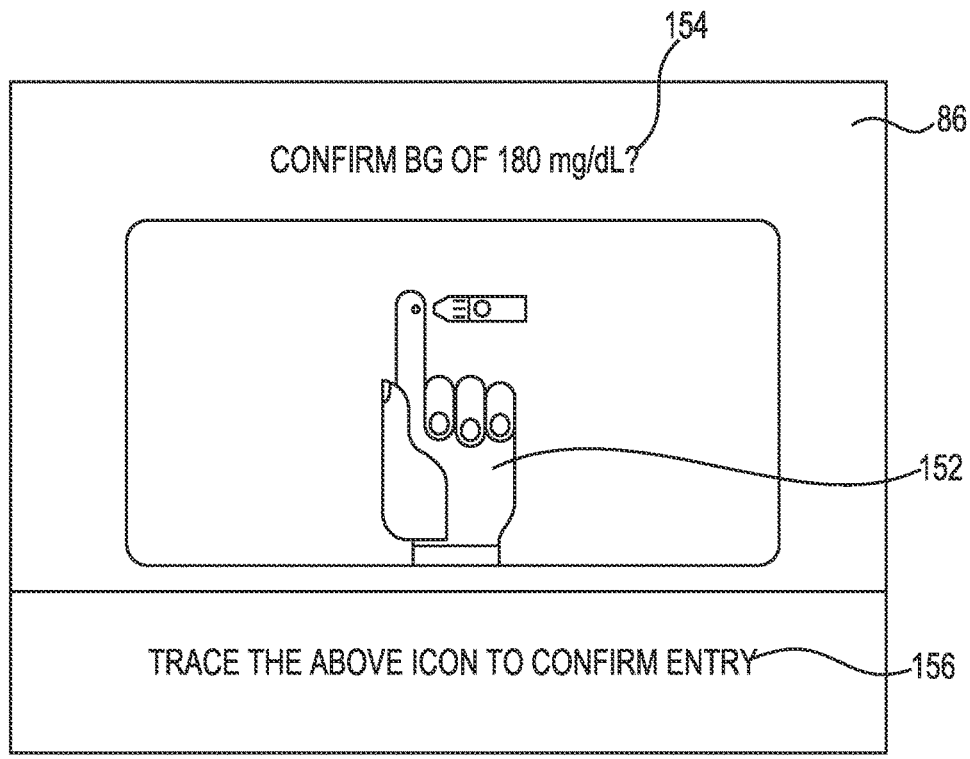
Figure 9B:
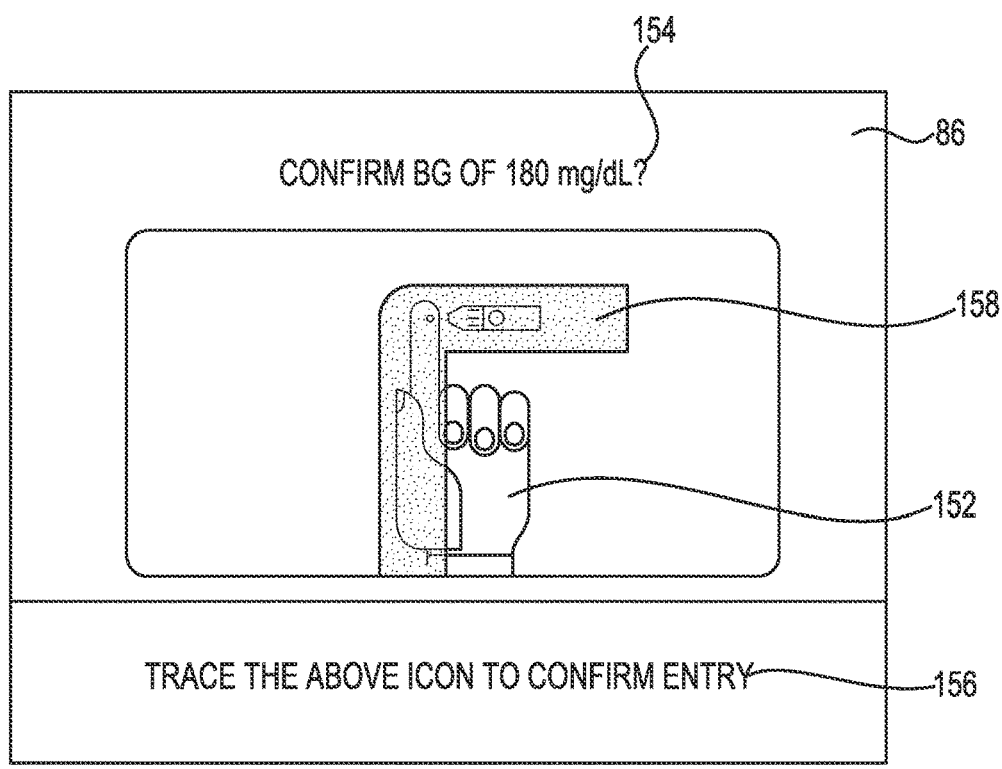

FIGS. 9A-9B depict an example of a blood glucose level confirmation screen 86 that can be used for confirming user entry of blood glucose values according to embodiments of the present invention. In this embodiment, a pictorial icon 152 representing a fingerstick for taking a blood sample from which a blood glucose level can be determined is utilized for providing the confirmation, but any other pictorial icon that could be considered to represent a blood sample or a blood glucose level could be utilized, as well as any of the aforementioned additional means by which confirmation can be prompted and/or received. As with the carbohydrate confirmation screen 84 in FIGS. 8A-8B, BG confirmation screen 86 can include, for example, confirmation text 154 detailing the parameter to be confirmed and instruction text 156 instructing the user how to provide the confirmation. FIG. 9B depicts one example of a tracing pattern 158 that can be used to provide the confirmation, but other patterns that trace portions of the icon could be utilized. In certain situations, such as in FIGS. 9A-9B where the tracing pattern of a given icon may not be intuitive to many users, an animation can be provided when the confirmation page is loaded showing the user how the icon should be traced to provide the confirmation. In various embodiments, BG confirmation screen 86 can be displayed after selecting the BG object 104 and entering a value using the keypad 120, as a first confirmation screen prior to bolus delivery in place of or in conjunction with first confirmation screen 80, as a second confirmation screen prior to bolus delivery in place of or in conjunction with second confirmation screen 81, or some combination thereof.

Figure 10A:
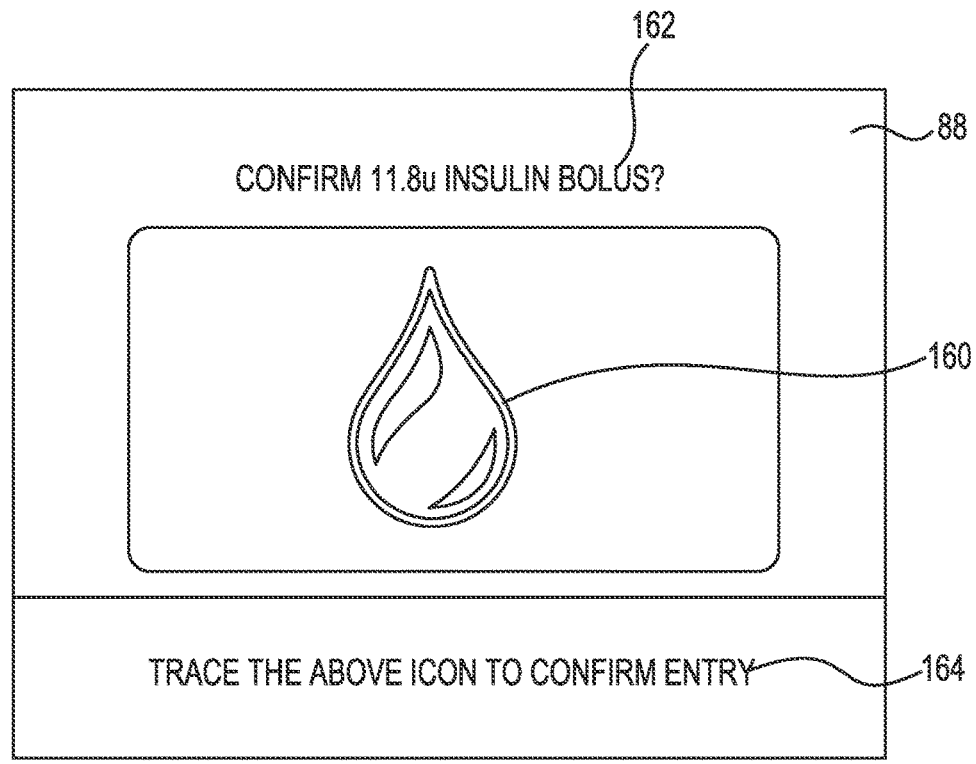
Figure 10B:
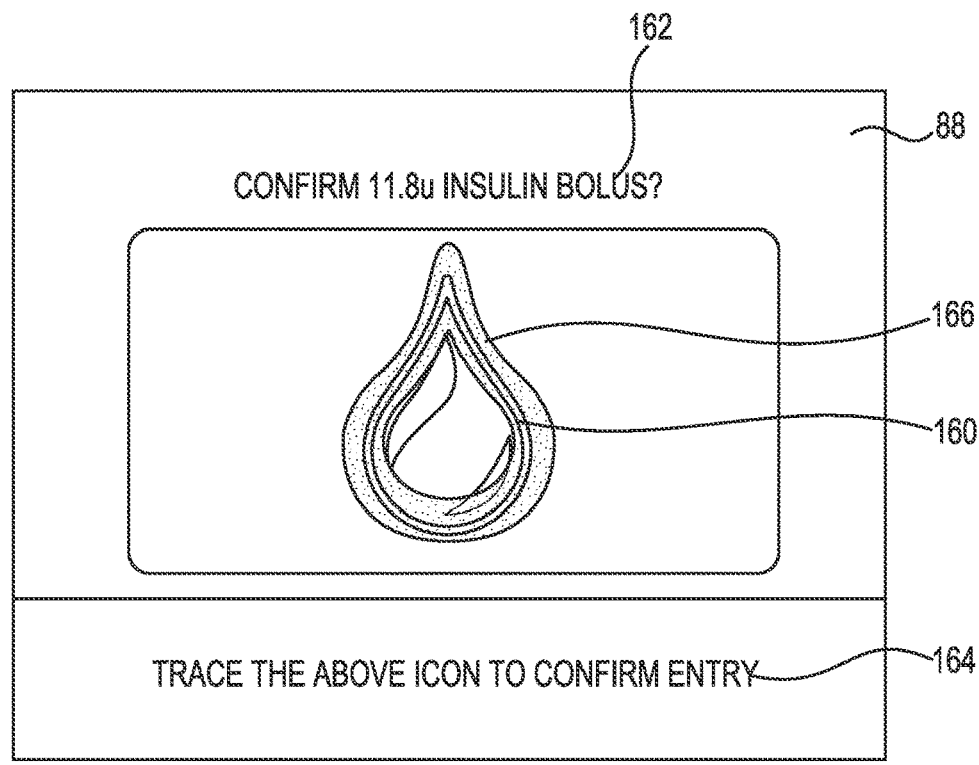

Referring now to FIGS. 10A-10B, there is depicted an example of an insulin bolus confirmation screen 88 that can be used for confirming an insulin or other medicament bolus according to embodiments of the present invention. In this embodiment, a pictorial icon 160 representing a droplet of insulin is utilized for providing the confirmation, but any other pictorial icon that could be considered to represent delivery of a medicament could be utilized, as well as any of the aforementioned additional means by which confirmation can be prompted and/or received. As with previous confirmation screens, bolus confirmation screen 88 can include, for example, confirmation text 162 detailing the parameter to be confirmed and instruction text 164 instructing the user how to provide the confirmation. FIG. 10B depicts one example of a tracing pattern 166 that can be used to provide the confirmation, but other patterns that trace portions of the icon could be utilized. In various embodiments, insulin bolus confirmation screen 88 can be displayed after selecting the INSULIN BOLUS object 103 and entering a value using the keypad 120, as a first confirmation screen prior to bolus delivery in place of or in conjunction with first confirmation screen 80, as a second confirmation screen prior to bolus delivery in place of or in conjunction with second confirmation screen 81, or some combination thereof.

Figure 12:
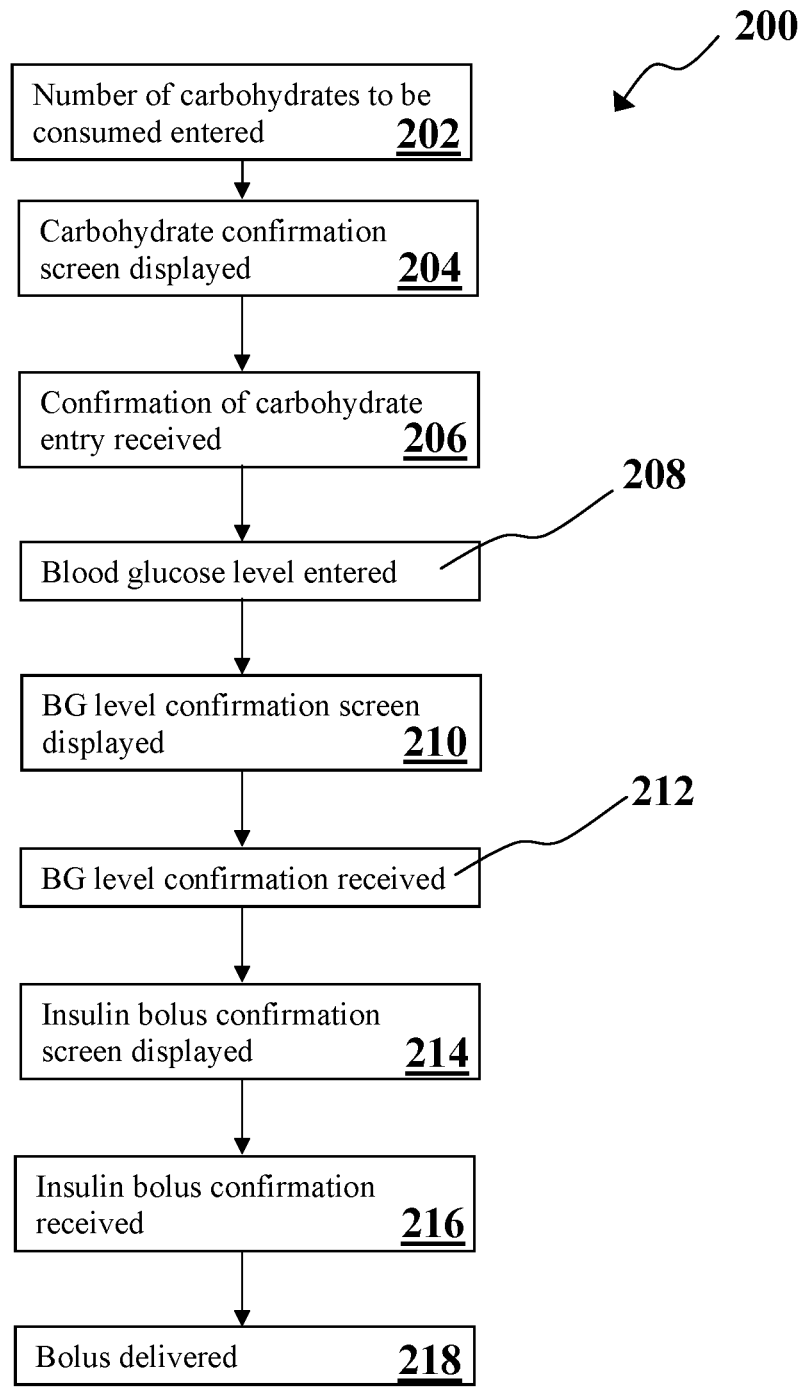
FIG. 12 is a flowchart depicting a method of confirming a bolus programming procedure according to an embodiment of the present invention.

In one embodiment, the carbohydrate entry confirmation screen 84 of FIGS. 8A-8B, the BG entry confirmation screen 86 of FIGS. 9A-9B, and the insulin bolus confirmation screen 10A-10B are employed sequentially during a bolus programming procedure to provide multiple confirmations ensuring that a user is properly programming the bolus and acknowledging confirmation of the proper programmed parameters. Referring to FIG. 12, such a confirmation method 200 includes the user entering a number of carbohydrates to be consumed at step 202 such as by, e.g., selecting a FOOD BOLUS object 102 as show in FIG. 4A and entering a value into a displayed keypad 120 as in FIG. 4B. Following entry of this carbohydrate value, the carbohydrate entry confirmation screen 84 is displayed at step 202. The user confirms entry of the number of carbohydrates at step 204 by tracing an icon relating to food or providing another confirmation as described herein.

Still referring to FIG. 12, next the user may enter a blood glucose level at step 206 such as by selecting a BG LEVEL object 104 as shown in FIG. 4B and entering a value into the displayed keypad 120. Following entry of the BG level, the BG confirmation screen 86 can be displayed at step 208. Entry of the BG level is then confirmed with the user tracing the corresponding icon on the confirmation screen at step 210, or providing another confirmation as described herein. With the number of carbohydrates and the user's BG level entered and confirmed, the total bolus to be delivered is known. As such, following confirmation of both the carbohydrate amount (or an insulin bolus amount as in FIG. 5A) and the BG level, the insulin bolus confirmation screen 86 is displayed at step 212. After a confirmation of the total insulin bolus is received at step 214 by tracing the corresponding icon or providing another confirmation as described herein, the insulin bolus can be delivered at step 216.

Through use of visual pictorial icons or images related to programmed parameters, the present invention requires the user to mentally associate the confirmation being provided with the specific parameter being confirmed, whereas in the prior art selection of the same "DONE" and "CONFIRM" objects to confirm all parameters provided no such association. In this manner, the risk of a user inadvertently entering a wrong parameter, e.g., typing in 180 for carbohydrates to be consumed rather than BG level, is substantially reduced, particularly in the case of embodiments such as that described with respect to FIG. 12 that require multiple such confirmations. Although described primarily with respect to entering parameters for programming a bolus of insulin, it should be understood that the described confirmation procedures requiring a user to trace an icon related to the programmed parameter or providing another associative confirmation as described herein can be applied to any programming aspect of such a pump, including, for example, programming a basal rate, programming operation limits, such as, e.g., a maximum bolus amount, programming alerts and reminders, etc.

Figure 11C:
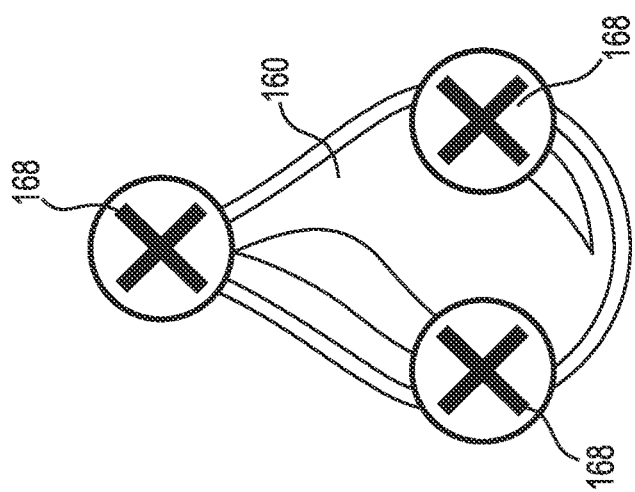
FIGS. 11A-11C depict exemplary icons used with confirmation screens according to embodiments of the present invention
Figure 11B:
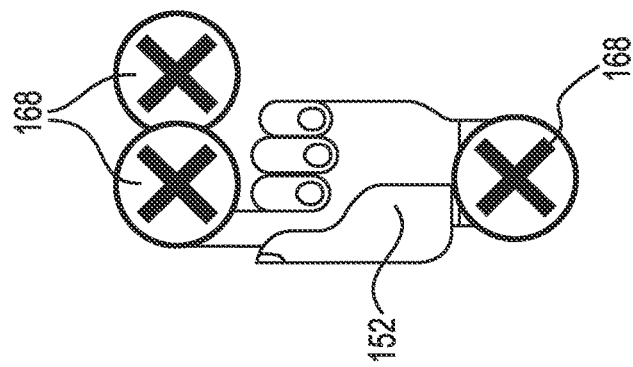
Figure 11A:
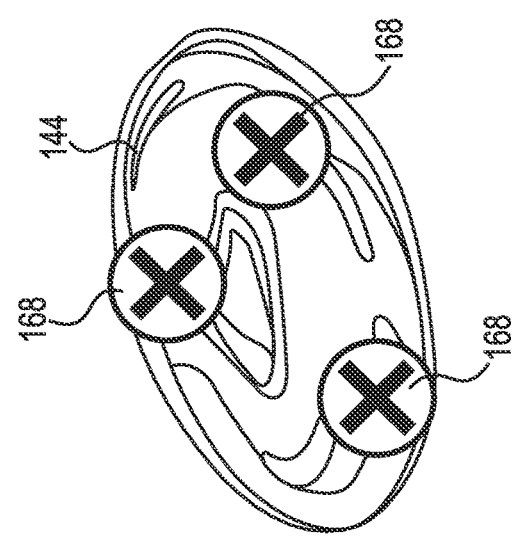

Some embodiments of touchscreens useable with the present invention may not support gesturing, such as tracing of icons displayed on the screen. FIGS. 11A-11C therefore depict alternative icons for carbohydrate confirmation 144, BG level confirmation 152 and insulin bolus confirmation 160 according to embodiments of the present invention. Rather than tracing these icons, confirmation is provided by selecting a plurality of, in this case three, discrete confirmation points 168 positioned on the icon relating to the parameter being confirmed. As show in FIGS. 11A-11C, these confirmation points 168 can be displayed for the user with confirmation icons, such as the circle "X" depicted in these figures. Alternatively, the user may be required to touch the icon in a designated number of discrete locations without specific icons dictating the locations of those touches. This embodiment therefore also provides a more substantial interaction with the confirmation screen reducing the likelihood of a user making a mistake as to which parameter was entered and is being confirmed. Various other interactions with icons displayed on a touchscreen as confirmations are also within the scope of the present invention, including, for example, a single touch of an icon and horizontal or vertical swiping of the icon.

As discussed above, it should be noted that confirmations within the scope of the present invention can include various other means of both prompting for and providing a confirmation, as described herein. For example, rather than or in addition to tracing a pattern of an icon, a user can be required to make a gesture, movement, reorientation, etc. of the device to provide the confirmation as measured by, e.g., a gyroscope or accelerometer within the device. In one embodiment, a video or graphic can be displayed on the device instructing the user as to the specific, e.g., gesture, required to confirm a specific parameter.

Another type of confirmation that can be employed in embodiments of the present invention can be an audible confirmation utilizing the speaker and microphone of the device. Such an embodiment can be particularly useful to aid blind or visually impaired users. The device can provide an audible prompt or series of prompts for confirmation related to the parameter(s) being confirmed. In response to this prompt or series of prompts, a specific voice confirmation or series of confirmations would be required to confirm the parameter(s) being programmed. Such audible confirmations could be used independently or in combination with any of the other confirmations described herein.

Confirmations that require biometric identification of the user are also contemplated. Such biometric confirmation can be provided along with or in addition to one or more other confirmations in order to ensure that a specifically authorized user, whose biometric data may be stored in memory, is programming the device, and can include, for example, a fingerprint, retinal scan, facial recognition or other technique or techniques. For example, when a user provides a touch confirmation, such as tracing an icon, the device could detect the user's fingerprint and compare it to saved fingerprint data for one or more authorized users. Alternatively, the biometric data can be provided in a discrete step before or following another confirmation, such as requiring a retinal scan to identify the user.

Embodiments utilizing remote control devices such as smartphones, as will be described herein, provide additional methods by which confirmations can be obtained or enhanced. For example, the camera of such a device can be utilized to provide the confirmation by, for example, taking a picture or covering the lens. A user could also be required to respond to a message using a smartphone such as, e.g. a text message providing a textual request for confirmation relating to the programmed parameter(s), with a specific confirmation response. Such an embodiment also provides a further authentication because the user's phone number would need to be associated with the medical device being programmed in order for the user to receive the confirmation text.

Figure 13B:
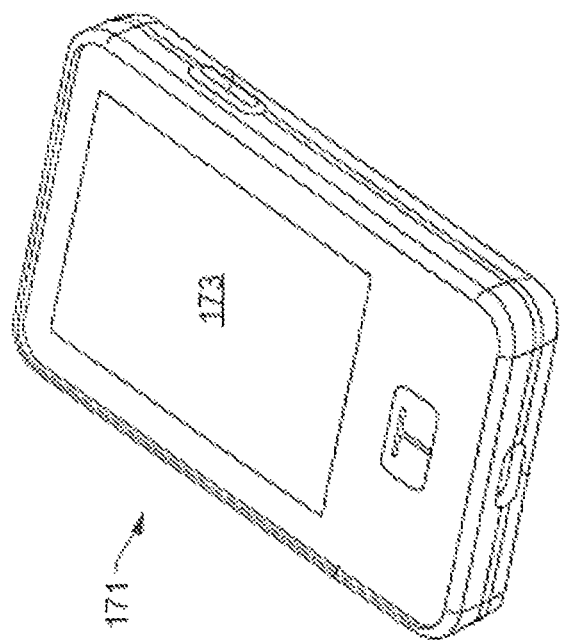
FIGS. 13A-13B depict touchscreen devices that can be utilized with embodiments of the present invention.
Figure 13A:
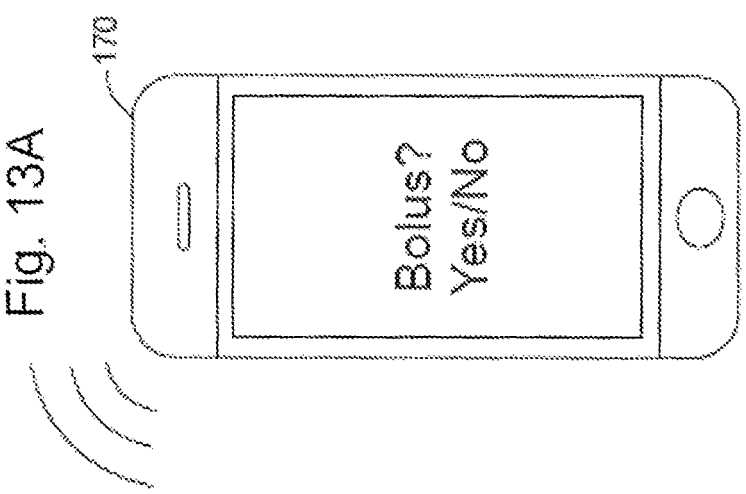

Although the present invention has been primarily described herein with respect to utilizing a touchscreen of a medical device such as an ambulatory infusion pump to program a bolus and provide confirmations using tracing patterns as described herein, it should be understood that the invention applies to any touchscreen device that can be utilized to send commands to an infusion pump. For example, FIGS. 13A-13B depict remote control devices that can be used to control delivery of medicament and transfer of data with an infusion pump via Bluetooth, Bluetooth low energy, mobile or Wi-Fi communication, for example, according to embodiments of the present invention. Such a remote control could include, for example, a dedicated remote controller 171 as shown in FIG. 13B, a mobile communication device 170 such as a smartphone as shown in FIG. 13A, a wearable electronic watch or electronic health or fitness monitor or a personal digital assistant (PDA), etc. or a tablet, laptop or personal computer. Such devices can include a touchscreen display 173 programmed to employ the confirmation procedures described herein. With respect to portable devices such as dedicated remote controller 171 and smartphone 170 that are often stored in a user's pocket, purse, etc., the complex confirmation procedures requiring more than a simple tap or press of the screen described herein provide the additional advantage of substantially reducing the possibility of an inadvertent confirmation occurring while the device is stored by the user.

In some embodiments, rather than the user touching the surface of a touch-screen by, e.g., tracing an icon by moving the user's finger directly on the screen, the system can incorporate pre-touch technologies for receiving confirmations. Examples of such technologies can be found in U.S. Pat. Nos. 9,501,218 and 9,535,598, each of which is incorporated by reference herein.

In one such embodiment, a user interface for providing confirmations as otherwise described herein may employ hover or pre-touch functionality. Hover or pre-touch functionality enables a user to select an icon without physically touching the screen, such as by placing the user's finger above the icon to be selected. Referring to FIGS. 8A-8B, for example, a system employing such functionality could receive a confirmation by way of a user situating the user's finger above the object 144 and then moving the finger in the tracing pattern 150 without actually touching the screen. In further embodiments, a hybrid touch and hover confirmation could be used, such that a first confirmation or first portion of a confirmation is submitted via touch and a second confirmation or second portion of a confirmation is submitted by hover/pre-touch.

In addition, although the embodiments herein are specifically described with respect to the delivery of insulin, delivery of other medicaments, singly or in combination with one another or with insulin, including, for example, glucagon, pramlintide, etc., as well as other applications are also contemplated. Device and method embodiments discussed herein may be used for pain medication, chemotherapy, iron chelation, immunoglobulin treatment, dextrose or saline IV delivery, treatment of various conditions including, e.g., pulmonary hypertension, or any other suitable indication or application. Non-medical applications are also contemplated.

Also incorporated herein by reference in their entirety are commonly owned U.S. Pat. Nos. 8,287,495; 8,408,421 8,448,824; 8,573,027; 8,650,937; 8,986,523; 9,173,998; 9,180,242; 9,180,243; 9,238,100; 9,242,043; and 9,335,910 commonly owned U.S. Patent Publication Nos. 2009/0287180; 2012/0123230; 2013/0053816; 2013/0159456; 2013/0324928; 2013/0331790; 2013/0332874; 2014/0273042; 2014/0276419; 2014/0276420; 2014/0276423; 2014/0276531; 2014/0276537; 2014/0276553; 2014/0276556 2014/0276569; 2014/0276570; 2014/0276574; 2014/0378898; 2015/0073337; 2015/0072613; 2015/0182693; 2015/0182694; 2015/0182695; 2016/0030669; and 2016/0082188 and commonly owned U.S. patent application Ser. Nos. 14/707,851 and 15/158,125 and commonly owned U.S. Provisional Application Ser. Nos. 61/911,576; 61/920,902; 61/920,914; 61/920,940; 62/139,275; 62/207,748; 62/256,398; 62/272,255; 62/300,410; and 62/352,164.

Further incorporated by reference herein in their entirety are U.S. Pat. Nos. 8,601,465; 8,502,662; 8,452,953; 8,451,230; 8,449,523; 8,444,595; 8,343,092; 8,285,328; 8,126,728; 8,117,481; 8,095,123; 7,999,674; 7,819,843; 7,782,192; 7,109,878; 6,997,920; 6,979,326; 6,936,029; 6,872,200; 6,813,519; 6,641,533; 6,554,798; 6,551,276; 6,295,506; and 5,665,065.

Various embodiments of systems, devices, and methods have been described herein. These embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed inventions.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of 35 U.S.C. § 112(f) are not to be invoked unless the specific terms "means for" or "step for" are recited in a claim.

The invention claimed is:

1. A method of delivering medicament to a user with a portable infusion pump, comprising:
   receiving user input programming a bolus delivery of medicament through a touchscreen display;
   displaying a first confirmation for the bolus delivery of medicament after receiving the user input programming the bolus delivery of medicament and determining an amount of the bolus delivery of medicament, the first confirmation displaying the amount of the bolus delivery of medicament and a touch-selectable first confirmation input comprising a pictorial icon having a shape related to the bolus delivery of medicament;
   receiving a touch-selection of the first confirmation input;
   displaying a second confirmation after receiving the first confirmation input, the second confirmation requiring a biometric authentication as a second confirmation input prior to delivering the bolus;
   receiving a biometric input as the second confirmation input;
   authenticating that the biometric input belongs to an authorized user;
   causing the bolus delivery of medicament to be delivered to the authorized user after authenticating the biometric input.

2. The method of claim 1, wherein receiving the biometric input includes receiving a fingerprint.

3. The method of claim 1, wherein receiving the biometric input includes performing a retinal scan.

4. The method of claim 1, wherein authenticating that the biometric input belongs to the authorized user includes facial recognition.

5. The method of claim 1, further comprising displaying instructional text instructing the user how to confirm the bolus delivery of medicament.

6. The method of claim 1, wherein receiving the touch-selection of the confirmation input includes receiving only a single touch of the confirmation input.

7. The method of claim 1, wherein the touchscreen display of the portable infusion pump system is a touchscreen display of the portable infusion pump.

8. The method of claim 1, wherein the touchscreen display of the portable infusion pump system is a touchscreen display of a remote control device configured to remotely control a portable infusion pump.

9. The method of claim 8, wherein the remote control device is a smartphone.

10. A method of delivering medicament to a user with a portable infusion pump, comprising:
- displaying a first confirmation for a bolus delivery of medicament to be delivered by a portable infusion pump following programming and determination of an amount of the bolus delivery of medicament, the first confirmation displaying an amount of the bolus delivery of medicament and a touch-selectable first confirmation input comprising a pictorial icon related to the bolus delivery of medicament;
- displaying a second confirmation after receiving the first confirmation input, the second confirmation requiring a biometric authentication as a second confirmation input to confirm the bolus;
- authenticating that a biometric input received in response to the second confirmation belongs to an authorized user; and
- causing the bolus delivery of medicament to be delivered to the authorized user after authenticating the biometric input.

11. The method of claim 10, wherein the received biometric input includes a fingerprint.

12. The method of claim 10, wherein the received biometric input includes a retinal scan.

13. The method of claim 10, wherein authenticating the biometric input includes facial recognition.

14. The method of claim 10, further comprising displaying instructional text instructing the user how to confirm the bolus delivery of medicament.

15. The method of claim 10, wherein receiving the touch-selection of the confirmation input includes receiving only a single touch of the confirmation icon.

16. The method of claim 10, wherein the touchscreen display of the portable infusion pump system is a touchscreen display of the portable infusion pump.

17. The method of claim 10, wherein the touchscreen display of the portable infusion pump system is a touchscreen display of a remote control device configured to remotely control a portable infusion pump.

18. The method of claim 17, wherein the remote control device is a smartphone.

* * * * *